United States Patent [19]

Hatton et al.

[11] Patent Number: 5,055,482

[45] Date of Patent: Oct. 8, 1991

[54] N-PHENYLPYRAZOL-4-YL ETHER DERIVATIVES

[75] Inventors: Leslie R. Hatton, Chelmsford; David W. Hawkins, Upminster; Richard G. Pennicard, Chelmsford; David A. Roberts, London, all of England

[73] Assignee: May & Baker Ltd., Dagenham, England

[21] Appl. No.: 375,959

[22] Filed: Jul. 6, 1989

[30] Foreign Application Priority Data

Jul. 6, 1988 [GB] United Kingdom ............... 8816096

[51] Int. Cl.$^5$ ............... A61K 31/415; A01N 43/56; C07D 401/04; C07D 403/04
[52] U.S. Cl. .................................. 514/407; 514/252; 514/236.5; 514/383; 514/359; 514/326; 548/266.2; 548/374; 548/375; 548/376; 548/377; 548/255; 548/266.2; 546/211; 544/371; 544/140
[58] Field of Search ............... 548/374, 375, 376, 255, 548/262, 377, 266.2; 546/211; 544/371, 140; 514/252, 236.5, 407, 383, 359, 326

[56] References Cited

U.S. PATENT DOCUMENTS 4,447,444  5/1984  Stähler et al. ..................... 548/376

FOREIGN PATENT DOCUMENTS 0280991  9/1988  European Pat. Off. .
0285947  10/1988  European Pat. Off. .
40/19958  6/1965  Japan .
WO87/03781  7/1987  PCT Int'l Appl. .

OTHER PUBLICATIONS

Pluempe et al., Chemical Abstracts vol. 68, entry 2846h (1968).
Soliman et al., Chemical Abstracts, vol. 97 entry 92195w (1982).
Kato et al., Chemical Abstracts, vol. 107, entry 176028g (1987).
Chem. Abs. 110:90608w, vol. 110, No. 11, Mar. 13, 1989, "Fruit Thinning Agents Containing Pyrazoles", p. 275, Col. 2 Kato et al.

Primary Examiner—John M. Ford
Attorney, Agent, or Firm—Burns, Doane, Swecker & Mathis

[57] ABSTRACT

An N-phenylpyrazol-4-yl ether derivative of the formula:

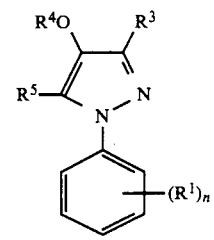

wherein $R^1$ represents halogen, alkyl or alkoxy unsubstituted or substituted by halogen, alkylthio or alkylsulphinyl substituted by one or more halogen atoms, nitro, cyano, or alkylsulphonyl unsubstituted or substituted by halogen and n is 1 to 5, $R^3$ represents hydrogen, halogen, cyano, nitro or alkyl group $R^2$ which may be unsubstituted or substituted by halogen, $R^4$ represents alkyl, alkenyl or alkynyl which is substituted by halogen, $R^5$ represents hydrogen or an amino group $NR^6R^7$ wherein $R^6$ and $R^7$ represent hydrogen, alkyl, formyl or alkanoyl (or $R^6$ and $R^7$ together form a 5 or 6 membered cyclic imide) which may be unsubstituted or substituted by halogen, or alkoxycarbonyl unsubstituted or substituted by halogen, or $R^5$ represents alkoxymethyleneamino unsubstituted or substituted on methylene by alkyl, or represents halogen, or pyrrol-1-yl, pyrazol-1-yl, 1,2,3-triazol-1-yl, 1,2,4-triazol-4-yl, piperidino, pyrrolidino, morpholino or N-alkylpiperazino optionally substituted by alkyl or phenyl and pesticidally acceptable acid addition salts thereof, possess arthropodicidal, nematocidal, anthelmintic and anti-protozoal activity.

9 Claims, No Drawings

N-PHENYLPYRAZOL-4-YL ETHER DERIVATIVES

This invention relates to N-phenylpyrazol-4-yl ether derivatives, to compositions containing them and to the use of N-phenylpyrazol-4-yl ether derivatives against arthropod, plant nematode, helminth and protozoan pests.

The present invention provides N-phenylpyrazol-4-yl ether derivatives of the general formula I, depicted hereinafter, wherein $R^1$ represents a halogen, i.e. fluorine, chlorine, bromine or iodine, atom, a straight- or branched-chain alkyl or alkoxy group containing from 1 to 4 carbon atoms which may be unsubstituted or substituted by one or more halogen atoms, e.g. a trifluoromethyl or trifluoromethoxy group), a straight- or branched-chain alkylthio or alkylsulphinyl group containing from 1 to 4 carbon atoms which is substituted by one or more halogen atoms (e.g. a trifluoromethylthio or trifluoromethylsulphinyl group), a nitro or cyano group or a straight- or branched-chain alkylsulphonyl group containing from 1 to 4 carbon atoms which may be unsubstituted or substituted by one or more halogen atoms (e.g. the trifluoromethylsulphonyl group), and n represents an integer from 1 to 5 inclusive, $R^3$ represents the hydrogen atom, a halogen, i.e. fluorine, chlorine, bromine or iodine, atom, a cyano or nitro group or a straight- or branched-chain alkyl group $R^2$ containing from 1 to 4 carbon atoms which may be unsubstituted or substituted by one or more halogen atoms, $R^4$ represents a straight- or branched-chain alkyl, alkenyl or alkynyl group containing up to 6 carbon atoms which is substituted by one or more halogen atoms (chosen from fluorine, chlorine, bromine or iodine and which may be the same or different), $R^5$ represents the hydrogen atom, or an amino group $NR^6R^7$ wherein $R^6$ and $R^7$, which may be the same or different, each represents a hydrogen atom or a straight- or branched-chain alkyl group containing from 1 to 6 carbon atoms, the formyl group, a straight- or branched-chain alkanoyl group containing from 2 to 7 carbon atoms (or $R^6$ and $R^7$ together form a 5 or 6 membered cyclic imide: with the nitrogen atom to which they are attached) which may be unsubstituted or substituted by one or more halogen atoms, or a straight- or branched-chain alkoxycarbonyl group containing from 2 to 7 carbon atoms which may be unsubstituted or substituted by one or more halogen atoms, or $R^5$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms, or represents a halogen i.e. fluorine, chlorine, bromine or iodine, atom or a group Het selected from pyrrol-1-yl, pyrazol-1-yl, 1,2,3-triazol-1-yl or 1,2,4-triazol-4-yl, piperidino, pyrrolidino, morpholino and N-alkylpiperazino which may be substituted by alkyl or phenyl groups, and pesticidally acceptable acid addition salts when $R^5$ is a piperidino, pyrrolidino, morpholino or N-alkylpiperazino group, which have valuable activity against arthropod, plant nematode, helminth and protozoan pests, more particularly by ingestion of the compound(s) of general formula I by the arthropods. When n represents an integer from 2 to 5 inclusive, atoms and groups represented by $R^1$ may be the same o different.

By the term "pesticidally acceptable acid addition salts" as used in this specification is meant salts of acids which are known and accepted in the art for the formulations of salts of biologically active compounds for agricultural or horticultural use. When intended for application to vertebrates to combat infection or infestation by arthropods, helminths or protozoa, the salts used will be non-toxic. By the term 'non-toxic' is meant salts with acids the anions of which are innocuous to the vertebrates at the doses administered and which do not vitiate the beneficial effects produced by the cation. Suitable salts of acids include salts of inorganic acids such a hydrochlorides, sulfates, phosphates and nitrates and salts of organic acids, for example acetates Preferred compounds of general formula I are those wherein $(R^1)n$ represents 2,4,6- trichloro, 2,6-dichloro-4-trifluoromethyl or 2,6-dichloro-4-trifluoromethoxy substitution of the phenyl group.

Preferably $R^4$ represents a straight- or branched-chain alkyl group of 1 to 4 carbon atoms or a straight- or branched-chain alkenyl or alkynyl group of 2 to 4 carbon atoms, each of which is substituted by one or more halogen atoms which may be the same or different for example a trifluoromethyl group or difluoromethyl group, and $R^3$ represents a halogen atom, or a nitro or preferably cyano group.

Preferably the substituted alkyl group $R^2$ is perhalogenated.

The following compounds of general formula I are of particular interest.
1. 3-Cyano-4-(2-chloro-1,1,2-trifluoroethoxy)-1-(2,6-dichloro-4-trifluoromethylphenyl)pyrazole.
2. 3-Cyano-1-(2,6-dichloro-4-trifluoromethylphenyl)-4-difluoromethoxypyrazole.
3. 1-(2,6-Dichloro-4-trifluoromethylphenyl)-4-difluoromethoxy-3-trifluoromethylpyrazole
4. 1-(2,6-Dichloro-4-trifluoromethylphenyl)-4-difluoromethoxy-3-methylpyrazole.
5. 5-Bromo-3-cyano-1-(2,6-dichloro-4-trifluoromethylphenyl)-4-difluoromethoxypyrazole.
6. 5-Amino-3-cyano-1-(2,6-dichloro-4-trifluoromethylphenyl)-4-difluoromethoxypyrazole.
7. 1-(2,6-Dichloro-4-trifluoromethylphenyl)-4-difluoromethoxy-3-nitropyrazole.

In experiments on activity against arthropods carried out on representative compounds, the following results (wherein ppm indicates the concentration of the compound in parts per million of the test solution applied) have been obtained:

Test 1

One or more of the dilutions of the compounds to be tested were made in 50% aqueous acetone.
a) Test species : *Plutella xylostella* (Diamond-back Moth) and Phaedon cochleariae (Mustar Beetle).
Turnip leaf discs were set in agar in petri-dishes and infected with 10 2nd instar larvae. Four replicate dishes were assigned to each treatment and were sprayed under a Potter Tower with the appropriate test dilution. Four or five days after treatment the dishes were removed from the constant temperature (25° C.) room in which they had been held and the mean percentage mortalities of larvae were determined. These data were corrected against the mortalities in dishes treated with 50% aqueous acetone alone which served as controls.

According to the above method (a) an application of 100 ppm of the following compounds was effective against the larvae of *Plutella xylostella*, producing at least 80% mortality.

Compound 1, 2, 6, 7

According to the above method (a) an application of 500 ppm of the following compounds was effective against the larvae of Phaedon cochleariae, producing at least 90% mortality.

Compound 3, 4, 5

In the following description when symbols appearing in formulae are not specifically defined it is to be understood that they are "as hereinbefore defined" in accordance with the first definition of each symbol in this specification. Within the process definitions, unless otherwise stated, amino refers to the unsubstituted amino group.

The compounds of general formula I can be prepared by the application or adaption of known methods (i.e. methods heretofore used or described in the chemical literature), followed where necessary by changing substituents with protection/deprotection of other substituents if necessary (e.g. acylation of amino groups later followed by hydrolysis of acylated amino to unsubstituted amino), for example as hereinafter described.

Compounds of general formula I, wherein $R^5$ represents a hydrogen or halogen atom or a $NR^6R^7$ group wherein $R^6$ and $R^7$ represent acetyl or alkyl groups may be prepared by reaction of a compound of general formula II, wherein $R^{5'}$ represents a hydrogen or halogen atom or a $NR^{6'}R^{7'}$ group wherein $R^{6'}$ and $R^{7'}$ represent acetyl or alkyl groups, or an alkali metal (i.e. sodium or potassium) salt thereof which may be formed in situ, with a reagent $R^4X'$ wherein $X'$ represents a halogen atom, or a compound of general formula $F_2lC\!=\!C(R^8)X^2$ (III) wherein $X^2$ represents a fluorine, chlorine or bromine atom and $R^8$ is as defined for $X^2$ or, represents the trifluoromethyl group, in the presence of a base for example triethylamine, pyridine or aqueous sodium hydroxide, in a solvent for example dioxan at a temperature from ambient to 100° C., when the reagent $R^4X'$ is a gas this may be bubbled into the reaction mixture, or the reaction may be carried out in an autoclave under autogeneous pressure. As will be apparent to those skilled in the art, reaction with compounds of general formula III may give rise, in addition to compounds of general formula I wherein $R^4$ represents a group of general formula $X^2CH(R^8)CF_2$— (IV) herein depicted, to compounds of general formula I wherein $R^4$ represents a group of general formula $X^2C(R^8)\!=\!CF$— (V), which may arise through elimination of a fluoride ion prior to work up of the reaction mixture.

Compounds of the general formula I wherein $R^4$ represents a perfluoroalkyl group containing from 1 to 4 carbon atoms and $R^5$ represents a hydrogen or halogen atom may be prepared by treatment of a compound of general formula VI wherein $R^{5'''}$ represents a hydrogen or halogen atom and $R^9$ represents the fluorine atom (prepared in situ by reaction of a compound of general formula VII with carbonyl fluoride at a temperature of 100° C.) or represents a perfluoroalkyl group containing from 1 to 3 carbon atoms with sulphur tetrafluoride at a temperature of 150°–180° C. with anhydrous hydrogen fluoride as catalyst in an autoclave. Intermediates of general formula VI may be prepared by reaction of compounds of general formula VII with the corresponding perfluoroacyl halide or anhydride, optionally in the presence of a base, such as pyridine and or a solvent, for example benzene at 0° C. to reflux.

Compounds of the general formula I wherein $R^4$ represents the trifluoromethyl group and $R^5$ represents a hydrogen or halogen atom may be prepared by reaction of a compound of general formula VII with an excess of carbon tetrachloride in the presence of anhydrous hydrogen fluoride in an autoclave at 100°–150° C. under autogeneous pressure.

Compounds of general formula I wherein $R^3$ represents the cyano group and $R^5$ represents a hydrogen or halogen atom or the amino group may be prepared by dehydrating an acid amide of general formula VIII wherein $R^{5''}$ represents the hydrogen or halogen atom or the amino group. The dehydration is generally effected by heating with a dehydrating agent, preferably phosphorus oxychloride at a temperature of from 50°–250° C. The corresponding acid (which may be prepared by hydrolysis of a compound of general formula XX) is reacted with a chlorinating agent preferably thionyl chloride at ambient to reflux temperature, followed by reaction of the intermediate acid chloride with ammonia to give the acid amide.

Compounds of the general formula I wherein $R^5$ represents the amino group and $R^3$ is other than the hydrogen atom or the nitro group may be prepared by reduction of compounds of general formula IX wherein $R^{3'}$ is as hereinbefore defined for $R^3$ but does not represent the hydrogen atom or the nitro group, with a mixture of hydrochloric acid and iron or stannous chloride or by catalytic hydrogenation in the presence of Raney Nickel, palladium on charcoal or Adams catalyst.

Intermediates of the general formula IX wherein $R^{3'}$ is as defined for $R^3$ other than the hydrogen atom and the nitro group, can be prepared by reaction of compounds of the general formula I wherein $R^3$ and $R^4$ are as and $R^5$ represents hydrogen, with a nitrating agent, preferably nitric acid optionally in the presence of sulfuric acid or nitric acid in a solvent such as acetic acid or acetic anhydride, at a temperature from 0° to 100° C.

Compounds of general formula I wherein $R^3$ represents a chlorine, bromine or iodine atom and $R^5$ represents a hydrogen, chlorine, bromine or iodine atom or the amino or the Het group, may be prepared by diazotization of a compound of general formula X wherein $R^{5'v}$ represents the hydrogen, chlorine, bromine or iodine atom or the amino or Het group, with an alkyl nitrite, preferably tertiary butyl nitrite, in the presence of a halogenating agent preferably anhydrous copper chloride, bromoform or iodine, at a temperature from 0° C. to 100° C.

Compound of the general formula I wherein $R^3$ represents the nitro group and $R^5$ represents hydrogen or halogen atom may be prepared by oxidation of a compound of general formula X wherein $R^{5'v}$ represents a hydrogen or halogen atom with trifluoroacetic peracid (which is prepared in situ from trifluoroacetic anhydride and hydrogen peroxide (85% w/w) in dichloromethane at room temperature to reflux.

Compounds of the general formula I wherein $R^3$ represents the trifluoromethyl group and $R^5$ represents a hydrogen or halogen atom or the amino group may be prepared by reaction of a carboxylic acid corresponding to general formula VIII, with a fluorinating agent, e.g. sulfur tetrafluoride optionally in the presence of anhydrous hydrogen fluoride at a temperature of 80°–150° C. carried out preferably in an autoclave under autogeneous pressure.

Compounds of general formula I wherein $R^3$ represents a methyl group and $R^5$ represents a hydrogen or halogen atom or the amino group may be prepared by reduction of a carboxylic acid corresponding to general formula VIII with a reducing agent, preferably borane-tetrahydrofuran complex, in a solvent preferably tetrahydrofuran, at a temperature from −30° C. to reflux.

Compounds of general formula I wherein $R^3$ represents the fluorine atom and $R^5$ represents a hydrogen or halogen atom may be prepared by diazotization of a compound of the general formula X wherein $R^{5'v}$ represents a hydrogen or halogen atom, using sodium nitrite in tetrafluoroboric acid and sulfuric acid at a temperature of −10° to +10° C. followed by photolysis in an excess of tetrafluoroboric acid at a temperature of −30° to +30° C.

Compounds of general formula I wherein $R^3$ represents the hydrogen atom and $R^5$ represents the hydrogen or halogen atom or the amino group may be prepared by decarboxylation of a compound of general formula XX with a mineral acid e.g. hydrobromic acid in acetic acid at reflux temperature.

Compounds of general formula I wherein $R^5$ represents a fluorine, chlorine, bromine or iodine atom may be prepared via diazotization of a compound of general formula I where $R^5$ represents an amino group as described above.

Compounds of general formula I wherein $R^3$ is other than alkyl group, $R^4$ is an alkyl group and $R^5$ is a chlorine, bromine or iodine atom may be prepared by reaction of the corresponding compound of general formula I wherein $R^5$ represents the hydrogen atom, with a halogenating agent, preferably N-halosuccinimide, in an inert solvent preferably carbon tetrachloride, at a temperature from ambient to reflux.

Compounds of general formula I wherein $R^5$ represents a group $NR^6R^7$ may be transformed into other compounds of general formula I wherein $R^5$ represents another group $NR^6R^7$. Compounds of general formula I which conform to general formula IB wherein $R^6$ represents an $R^{10}C(=O)-$ group, wherein $R^{10}$ represents a straight- or branched-chain alkyl or alkoxy group containing from 1 to 6 carbon atoms, and $R^7$ represents a hydrogen atom or an $R^{10}C(=O)-$ group which is identical to the group $R^{10}C(=O)-$ represented by $R^6$ or $-NR^6R^7$ represents a cyclic imide as hereinbefore defined, may be prepared by the reaction of a compound of general formula I wherein $R^5$ represents the unsubstituted amino group, or an alkali metal salt thereof, with a compound of the general formula:

$$R^{10}COX^3 \qquad XI$$

wherein $X^3$ represents a chlorine or bromine atom, or with a compound of the general formula:

$$(R^{10}CO)_2O \qquad XII$$

or with a dicarboxylic acid derivative. The reaction may be conducted in the absence or presence of an inert organic solvent, for example acetonitrile, tetrahydrofuran, a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction medium, to give a compound of general formula IB wherein $R^6$ represents an $R^{10}C(=O)-$ group wherein $R^{10}$ is as hereinbefore defined and  represents a hydrogen atom or an $R^{10}C(=O)-$ group, depending upon the reaction conditions chosen and/or the use of an excess of the compound of general formula XI or XII, or $-NR^6R^7$ represents a cyclic imide as hereinbefore defined.

Compounds of general formula IB wherein $R^6$ represents a formyl group and $R^7$ represents a hydrogen atom or a formyl group, may be prepared by the reaction of a compound of general formula I, wherein $R^5$ represents the unsubstituted amino group with formylacetic anhydride. Formylacetic anhydride may be prepared from formic acid and acetic anhydride and the reaction with the compound of general formula I may be conducted in the absence or presence of an inert organic solvent, for example a ketone, e.g. acetone, or an aromatic hydrocarbon, e.g. benzene or toluene, and optionally in the presence of an acid-binding agent, for example pyridine, triethylamine or an alkali metal, e.g. sodium or potassium, carbonate or bicarbonate, at a temperature from 0° C. to the reflux temperature of the reaction mixture, to give a compound of general formula IB wherein $R^6$ represents a formyl group and $R^7$ represents a hydrogen atom or a formyl group, depending upon the reaction conditions chosen and/or the use of an excess of formylacetic anhydride.

Compounds of general formula IB wherein $R^6$ represents a formyl group or a group $R^{10}C(=O)-$  and $R^7$ represents a hydrogen atom may be prepared by the selective removal by hydrolysis of an $R^{10}C(=O)-$ group or a formyl group from a compound of general formula IB wherein $R^6$ and $R^7$ both represent a $R^{10}C(=O)$ group or a formyl group. Hydrolysis is effected under mild conditions, for example by treatment with an aqueous-ethanolic solution or suspension of an alkali metal, e.g. sodium or potassium, bicarbonate, or with aqueous ammonia.

Compounds of general formula IB wherein $R^6$ represents a straight- or branched-chain alkoxycarbonyl group containing from 2 to 7 carbon atoms which is unsubstituted or substituted by one or more halogen atoms, and $R^7$ represents a hydrogen atom may be prepared by the reaction of a compound of the general formula XIII wherein $R^{11}$ represents an alkoxycarbonyl group $R^{12}C(=Ol)$, wherein $R^{12}$ represents a straight- or branched-chain alkoxy group containing from 1 to 6 carbon atoms (which is unsubstituted or substituted by one or more halogen atoms) or a phenoxy group, with a compound of the general formula:

$$R^{12}H \qquad XIV$$

to replace a first group represented by the symbol $R^{11}$ by a hydrogen atom, and to replace the second group represented by the symbol $R^{11}$ by an alkoxycarbonyl group when $R^{11}$ represents a phenoxycarbonyl group, or, if desired, to replace the second group represented by the symbol $R^{11}$ by another alkoxycarbonyl group when $R^{11}$ in formula XIII represents an alkoxycarbonyl group. As will be apparent to those skilled in the art, the desired compound of general formula IB is obtained by selection of the appropriate compounds of general formulae XIII and XIV. The reaction may be effected in water or an inert aqueous-organic or organic solvent, for example an alkanol containing 1 to 4 carbon atoms, e.g. ethanol, or an aromatic hydrocarbon, e.g. benzene or toluene, or which is preferably an excess of the compound of general formula XIV, at a temperature from ambient temperature to the reflux temperature of the reaction mixture and, if necessary, at elevated pressure, and optionally in the presence of a base, for example an alkali metal alkoxide, e.g. of the compound of general formula XIV.

Compounds of general formula IB wherein $R^6$ and $R^7$, which may be the same or different, each represents a formyl group or a $R^{10}C(=O)$— group, may be prepared by the reaction of an alkali metal, e.g. sodium or potassium, derivative of a compound of general formula IB wherein $R^6$ represents a group $R^{10}C(=O)$— as hereinbefore defined, or a formyl group, and $R^7$ represents a hydrogen atom with formylacetic anhydride or a compound of general formula XI. Reaction may be effected in an inert aprotic solvent, e.g. dimethylformamide, at a temperature from laboratory temperature to the reflux temperature of the reaction mixture.

Alkali metal derivatives of compounds of general formula I (wherein $R^5$ represents the unsubstituted amino group) or IB wherein $R^7$ represents a hydrogen atom may be prepared in situ by reaction with an alkali metal, e.g. sodium or potassium, hydride, in an inert aprotic solvent, e.g. dimethylformamide, at a temperature from laboratory temperature to the reflux temperature of the reaction mixture.

Compounds of general formula XIII wherein $R^{11}$ represents a group $R^{12}C(=O)$—, may be prepared as hereinbefore described. Compounds of general formula XIII wherein $R^{12}$ represents a phenoxycarbonyl group may be prepared by the reaction of a compound of general formula I (wherein $R^5$ represents the unsubstituted amino group), with phenyl chloroformate using the reaction conditions hereinbefore described for the reaction of a compound of general formula I with a compound of formula XI.

Compounds of general formula IB wherein $R^6$ represents a group $R^{13}$ which represents a straight- or branched-chain alkyl group containing from 1 to 6 carbon atoms and $R^7$ represents a hydrogen atom may be prepared by the removal of the group $R^{10}C(=O)$— of a compound of the general formula IB, wherein $R^6$ represents a group $R^{13}$ and $R^7$ represents a group $R^{10}C(=O)$—. Removal of the group $R^{10}C(=O)$— may be effected by selective hydrolysis under mild conditions, for example by treatment with an alkali metal, e.g. sodium or potassium, hydroxide in water or an inert organic or aqueous-organic solvent, for example a lower alkanol, e.g. methanol, or a mixture of water and lower alkanol, at a temperature from laboratory temperature up to the reflux temperature of the reaction mixture.

Compounds of general formula IB, wherein $R^6$ represents a group $R^{13}$ and $R^7$ represents a group $R^{10}C(=O)$—, may be prepared by reaction of a compound of general formula IB wherein $R^6$ represents a hydrogen atom and $R^7$ represents a group $R^{10}C(=O)$—, or an alkali metal, e.g. sodium or potassium, derivative thereof, with a compound of the general formula:

$$R^{13}X^4 \qquad \qquad XV$$

wherein $X^4$ represents a chlorine, bromine or iodine atom. Reaction may be effected in an inert organic solvent, e.g. dichloromethane, tetrahydrofuran or dimethylformamide, at a temperature from laboratory temperature up to the reflux temperature of the reaction mixture and, when a compound in which $R^6$ represents a hydrogen atom is used, in the presence of a base, e.g. Triton B; or by reaction of a compound of general formula IB wherein $R^6$ represents the hydrogen atom and $R^7$ represents a group $R^{13}$ with a compound of general formula XI or XII.

Compounds of general formula I wherein $R^5$ represents an N-(alkyl)-N- formylamino group as hereinbefore described may be prepared in a similar manner to the process above using, where appropriate, formylacetic anhydride instead of a compound of general formula XI or XII.

Compounds of general formula IB wherein one of $R^6$ and $R^7$ or both of $R^6$ and $R^7$ represent a straight- or branched-chain alkyl group containing from 1 to 6 carbon atoms, groups represented by $R^6$ and $R^7$ being identical, may be prepared by reaction of a compound of general formula I, wherein $R^5$ represents the unsubstituted amino group, or an alkali metal, e.g. sodium or potassium, derivative thereof, with a compound of general formula XV, in the absence or presence of an inert organic solvent, for example an aromatic hydrocarbon, e.g. benzene or toluene, chloroform, dichloromethane, tetrahydrofuran or dimethylformamide, and optionally in the presence of an acid-binding agent, for example pyridine, triethylamine or an alkali metal, e.g. sodium or potassium, bicarbonate, at a temperature from 0° C. up to the reflux temperature of the reaction mixture.

Compounds of general formula I wherein $R^5$ represents a straight- or branched-chain alkoxymethyleneamino group containing from 2 to 5 carbon atoms which may be unsubstituted or substituted on methylene by a straight- or branched-chain alkyl group containing from 1 to 4 carbon atoms may be prepared by the reaction of a compound of general formula I (wherein $R^5$ represents the unsubstituted amino group) with a trisalkoxyalkane in the presence of an acidic catalyst, e.g. p-toluenesulphonic acid, at a temperature from ambient temperature to the reflux temperature of the reaction mixture.

Compounds of general formula I wherein $R^5$ represents —$NHCH_2R^{14}$ wherein $R^{14}$ represents the hydrogen atom or a straight- or branched-chain alkyl group containing from 1 to 4 carbon atoms may be prepared by reaction of a compound of general formula I wherein $R^5$ represents —$N=C(OR^{15})R^{14}$ wherein $R^{15}$ represents a straight- or branched-chain alkyl group containing from 1 to 4 carbon atoms with a reducing agent, preferably sodium borohydride. The reaction may be effected in an inert organic solvent, ethanol or methanol being preferred, at a temperature from 0° C. to the reflux temperature of the reaction mixture.

Compounds of the general formula I wherein $R^5$ represents an optionally substituted pyrrol-1-yl, pyrazol-1-yl, 1,2,3-triazol-1-yl or 1,2,4-triazol-4-yl group may be prepared by reaction of a compound of the (i) general formula I wherein $R^5$ represents the amino group with the corresponding 1,4-diketone, or an acetal or ketal derivative thereof, or with an optionally substituted 2,5-dimethoxytetrahydrofuran.

(ii) general formula XVI with the corresponding 1,3-diketone, or an acetal or ketal derivative thereof;

(iii) general formula XVII with the corresponding acetylene;

(iv) general formula I wherein $R^5$ represents the amino group with the corresponding diacylhydrazine.

The reactions may be carried out in an inert solvent, for example dioxan optionally in the presence of an acid catalyst, at ambient to reflux temperature. Intermediates of general formulae XVI and XVII may be prepared from compounds of general formula I wherein $R^5$ represents the amino group, by diazotization with sodium nitrite in a mineral acid followed by either reduction with a mixture of stannous chloride and hydrochloric acid or reaction with sodium azide, respectively.

Compounds of general formula II wherein $R^3$ represents the cyano group, trifluoromethyl or methyl group or hydrogen atom, and $R^{5'}$ represents the hydrogen atom, may be prepared from a compound of general formula XVIII wherein $R^{16}$ represents an alkyl group containing from 1 to 8 carbon atoms preferably methyl or ethyl, by modification of the carboxylic ester group in a similar manner to that hereinbefore described, optionally employing known protecting groups on the hydroxyl function.

Compounds of general formula I, wherein $R^5$ represents a pyrrolidino, piperidino, morpholino or N-alkylpiperazino group may be prepared by treatment of a compound of general formula I, where $R^5$ represents the amino group, with a compound of general formula $HalCH_2—X—CH_2Hal$ wherein X is the ethylene, propylene, 2-oxapropylene or N-alkyl-2-azapropylene group respectively in the presence of a base, preferably sodium hydride, in an inert polar solvent such as dioxan at a temperature between ambient and the boiling point of the solvent.

Compounds of general formula XVIII can be prepared by cyclization of intermediates of general formula XIX with a base, preferably potassium acetate, in an inert alkanol (e.g. ethanol) at a temperature from ambient to reflux. Intermediates of general formula XIX can be prepared by diazotization of the appropriate aniline with a solution of sodium nitrite in a mineral acid e.g. a mixture of acetic and sulfuric acid at a temperature from 0° to 60° C. then reacting with a compound of formula $ClCH_2COCH_2CO_2R^{16}$ wherein $R^{16}$ is preferably ethyl, in the presence of an inert solvent i.e. acetic acid and water, optionally in the presence of sodium acetate at a temperature of 0 to 40° C.

Compounds of general formula X wherein $R^{5'v}$ represents the hydrogen atom can be prepared by performing a Curtius rearrangement of the corresponding acid azide by heating in an inert solvent such as toluene at a temperature from 50° to 150° C. to give an isocyanate which is then reacted with tertiary butanol to give a carbamate which in turn is hydrolyzed using dilute hydrochloric acid in ethanol at a temperature from ambient to reflux. The intermediate acid azide may be prepared from compounds of general formula XX wherein $R^{5''}$ represents the hydrogen atom by reaction of the corresponding carboxylic acid (prepared by hydrolysis) with an azide transfer agent preferably diphenylphosphonylazide in a solvent such as dimethyl formamide in the presence of triethylamine at a temperature from ambient to 100° C.

Compounds of general formula XX may be prepared by etherification of compounds of general formula XVIII.

Intermediates of general formula II wherein $R^3$ represents a nitro, cyano or methyl group, and $R^{5'}$ represents the hydrogen atom may be prepared by cyclization of intermediates of general formula XXI wherein Y represents a chlorine or bromine atom and $R^{3''}$ represents a methyl, carbamoyl, nitro or cyano group as hereinbefore described for preparation of compounds of general formula XVIII. Intermediates of general formula XXI wherein Y represents a chlorine or bromine atom and $R^{3''}$ represents a methyl, carbamoyl, nitro or cyano group may be prepared by halogenation of intermediates corresponding to general formula XXI wherein Y is replaced by the hydrogen atom by reaction with a molar equivalent of chlorine or bromine in acetic acid at reflux. Such compounds can be prepared by reaction of an aryl diazonium salt with 2-acetylpropionaldehyde, acetoacetamide, nitroacetone or acetylacetonitrile as hereinbefore described for the preparation of compounds of general formula XIX.

Compounds of general formula II wherein $R^3$ is an alkyl or haloalkyl group or a halogen atom other than iodine, or a hydrogen atom and $R^{5'}$ is the hydrogen atom or diacetylamino group, may be prepared by reaction of a compound of general formula XXII (after diacetylation of the amino group if necessary) with methyl magnesium iodide in a solvent, preferably toluene, at a temperature of 50° to 100° C., followed by treatment of the intermediate dimethylcarbinol (or isopropylidene compound) with a mixture of hydrogen peroxide (30% w/w) and sulfuric acid at ambient temperature and subsequent rearrangement of the peroxide with sulfuric acid (80%) at ambient temperature.

Intermediates of general formula XXII wherein $R^{3'''}$ is an alkyl or haloalkyl group or a halogen atom other than iodine, or a hydrogen atom and $R^{5''}$ represents the amino group may be prepared by reaction of a compound of general formula XXIII where $R^{17}$ is a halogen atom other than iodine, or an ethoxy or hydroxy group with an appropriately substituted phenyl hydrazine (or acid addition salt thereof) of general formula XXIV in an inert solvent for example ethanol or acetic acid at a temperature from ambient to reflux optionally in the presence of a base i.e. potassium carbonate or triethylamine. The intermediate compound of general formula XXV may precipitate during the course of the reaction, this may be isolated and subsequently cyclized by heating in an inert solvent e.g. 2-ethoxyethanol or acetic acid at a temperature from ambient to reflux optionally in the presence of a base e.g. potassium acetate.

The intermediates of general formula XXII wherein $R^{5''}$ represents the hydrogen atom may be prepared from the corresponding compounds wherein $R^{5''}$ represents the amino group, by reaction with tertiary butyl nitrite in tetrahydrofuran at ambient to reflux temperature.

Compounds of general formula XX wherein $R^{5''}$ represents the amino group may be prepared by nitration and subsequent reduction of a compound of general formula XX wherein $R^{5''}$ represents a hydrogen atom, in similar manner to that hereinbefore described.

Compounds of general formula XXI and XXII can be prepared by methods known per se.

It will be appreciated that in the preparation of compounds of general formula I the foregoing processes or adaptations thereof may be performed in an appropriate combination to achieve the compound sought.

The following Examples and reference examples illustrate the preparation of compounds of general formula and the preparation of intermediates.

In the following examples and reference examples, dry-column chromatography was performed with silica gel 60G as the stationary phase and medium pressure chromatography was performed with silica gel (40/60 flash silica) at a pressure of 6.8 $Nm^{-2}$l.

EXAMPLE 1

Compound 1

A mixture of (RS)-3-carbamoyl-4-(2-chloro-1,1,2-trifluoroethoxy)-1-(2,6-dichloro-4-trifluoromethylphenyl)pyrazole (0.75g) and phosphorus oxychloride (15ml) was heated at 80° C. for 6 hours. Water (100ml) and dichloromethane (50ml) were added to the cooled mixture and the layers were separated. The aqueous layer was extracted with dichloromethane (2x50ml) and the combined organic layers were washed with aqueous sodium hydrogen carbonate solution (1M; 30ml), dried over magnesium sulfate, and evaporated to give (RS)-4-(2-chloro-1,1,2-trifluoroethoxy)-1-(2,6-dichloro-4-trifluoromethylphenyl)-3-cyanopyrazole (0.4g) as an off-white crystalline solid, m.p. 99°–101° C.

EXAMPLE 2

Compound 2

By proceeding in a similar manner to example 1 but using 3-carbamoyl-1-(2,6-dichloro-4-trifluoromethylphenyl)-4-difluoromethoxypyrazole in place of (RS)-3-carbamoyl-4-(2-chloro-1,1,2-trifluoroethoxy)-1-(2,6-dichloro-4-trifluoromethylphenyl)pyrazole, there was obtained 3-cyano-1-(2,6-dichloro-4-trifluoromethylphenyl)-4-difluoromethoxypyrazole as a beige solid, m.p. 85°–87° C.

EXAMPLE 3

Compound 3

1-(2,6-Dichloro-4-trifluoromethylphenyl)-4-hydroxy-3-trifluoromethylpyrazole (1.0g) was added to a stirred mixture of aqueous sodium hydroxide solution (2M; 15 ml) and dioxan (15 ml). The mixture was heated to 50°–60° C. and stirred under an atmosphere of chlorodifluoromethane. After 24 hours, the solvent was evaporated. The residue was taken up in dilute aqueous sodium hydroxide solution (2M) and extracted with ether (3×30 ml) and the combined organic layers were washed with water (20 ml), dried over magnesium sulfate, filtered and evaporated to give a solid (0.6 g). The residue was purified by dry-column chromatography (eluant hexane:ether 3:1) to give 1-(2,6-dichloro-4-trifluoromethylphenyl)-4-difluoromethoxy-3-trifluoromethylpyrazole (0.55 g), as a colorless solid, m.p. 55.5°–58° C.

REFERENCE EXAMPLE 1

(RS)-3-Carboxy-4-(2-chloro-1,1,2-trifluoroethoxy)-1-(2,6-dichloro-4-trifluoromethylphenyl)pyrazole (1.1 g) was dissolved in toluene (50 ml), the solution was heated to reflux, and 10 ml of the solvent were distilled azeotropically. Thionyl chloride (5 ml) was added to the residue and the mixture was refluxed for 3 hours and evaporated. Toluene (20 ml) was added to the residue and the resulting solution was evaporated to dryness. The residue was dissolved in ether (25 ml), aqueous ammonia (d. 0.88; 30 ml) was added, and the mixture was stirred vigorously for 18 hours. The layers were separated and the aqueous layer was extracted with ether (30 ml). The combined ether layers were washed with brine (30 ml), dried over magnesium sulfate and evaporated (1.0 g). The residue was purified by dry-column chromatography (eluant ether:hexane 1:1 then pure ether) to give (RS)-3-carbamoyl-4-(2-chloro-1,1,2-trifluoroethoxy)-1-(2,6-dichloro-4-trifluoromethylphenyl)pyrazole (0.8 g) as an off-white solid m.p. 163.5°–16.5° C. By proceeding in a similar manner but using 3-carboxy-1-(2,6-dichloro-4-trifluoromethylphenyl)-4-difluoromethoxypyrazole, in place of (RS)-3-Carboxy-4-(2-chloro-1,1,2-trifluoroethoxy)-1-(2,6-dichloro-4-trifluoromethylphenyl)pyrazole, there was obtained 3-carbamoyl-1-(2,6-dichloro-4-trifluoromethylphenyl)-4-difluoromethoxypyrazole as a yellow-white solid, m.p. 145°–146.5° C.

REFERENCE EXAMPLE 2

A mixture of (RS)-3-carboethoxy-4-(2-chloro-1,1,2-trifluoroethoxy)-1-(2,6-dichloro-4-trifluoromethylphenyl)pyrazole 5 (0.95 g), aqueous sodium hydroxide solution (2M; 20 ml) and methanol (20 ml) was stirred at room temperature for 20 hours. The solution was acidified with hydrochloric acid (2M), diluted with water (50 ml) and extracted with ether (2×30 ml). The combined extracts were dried over magnesium sulfate and evaporated to give (RS)-3-carboxy-4-(2-chloro-1,1,2-trifluoroethoxy)-1-(2,6-dichloro-4-trifluoromethylphenyl)pyrazole (0.7 g) as a yellow solid, m.p. 149°–159° C.

REFERENCE EXAMPLE 3

3-Carboethoxy-1-(2,6-dichloro-4-trifluoromethylphenyl)-4-hydroxypyrazole (2.0 g) was added to a stirred suspension of sodium hydride (80% dispersion in oil; 0.2 g) in dry dioxan (20 ml). When the resultant effervescence had subsided, the solution was heated to 80°–900 °C. and stirred while 2-chloro-1,1,2-trifluoroethylene was passed through. After 6 hours, the reaction was complete and the solvent was evaporated to dryness. The residue was dissolved in dilute hydrochloric acid (2M; 10 ml) and dichloromethane (20 ml) and the layers were separated. The aqueous layer was extracted with dichloromethane (30 ml) and the combined organic layers were washed with water (20 ml), dried over magnesium sulfate, filtered and evaporated. The residue was purified by dry-column chromatography (eluant ether:hexane 1:3) to give (RS)-3-carboethoxy-4-(2-chloro-1,1,2-trifluoroethoxy)-1-(2,6-dichloro-4-trifluoromethylphenyl)pyrazole (1.0 g). This was recrystallised from hexane to yield colorless needles, m.p. 105°–106.5° C.

REFERENCE EXAMPLE 4

By proceeding in a similar manner to Reference Examples 2 and 3 but using 3-Carboethoxy-1-(2,6-dichloro-4-trifluoromethylphenyl)-4-hydroxypyrazole in place of 1-(2,6-dichloro-4-trifluoromethylphenyl)-4-hydroxy-3-trifluoromethylpyrazole, there was obtained 3-carboxy-1-(2,6-dichloro-4-trifluoromethylphenyl)-4-difluoromethoxypyrazole as a pale yellow solid, m.p. 180°–183° C.

REFERENCE EXAMPLE 5

Ethyl 2-(2,6-dichloro-4-trifluoromethylphenylazo)-4-chloroacetoacetate (52.7 g) was dissolved in ethanol (650 ml) and heated to reflux. Potassium acetate (11.2 g) was added portionwise and the reaction mixture was boiled for 1 hour and allowed to cool, and the solvent was evaporated. The residue was dissolved in dichloromethane (500 ml), washed with water (2×150 ml), dried over magnesium sulfate, filtered and evaporated. The residue was triturated with hexane, filtered and dried to give 3-carboethoxy-1-(2,6-dichloro-4-trifluoromethylphenyl)-4-hydroxypyrazole (34.0 g) as a light brown solid, m.p. 140°-143° C.

REFERENCE EXAMPLE 6

Sodium nitrite (9.6 g) was warmed in concentrated sulfuric acid (40 ml) to form a homogeneous mixture. The solution was allowed to cool to room temperature and a solution of 2,6-dichloro-4-trifluoromethylaniline (described in European Patent Publication 23,100:30.0 g) in glacial acetic acid (230 ml) was added dropwise, with stirring and efficient external cooling to keep the temperature below 30° C. The reaction mixture was heated at 55°-60° C. for 45 minutes, allowed to cool to room temperature, and added dropwise to a stirred solution of ethyl 4-chloroacetoacetate 21.6 g) in glacial acetic acid (100 ml) and water (200 ml). Sodium acetate (122 g) and a further 200 ml of water were added. The resultant precipitate was filtered and the filter cake was washed thoroughly with water, sucked dry and dried in a vacuum desiccator to give ethyl 2-(2,6-dichloro-4-trifluoromethylphenylazo)-4-chloroacetoacetate as a light brow solid (52.7 g), m.p. 62°-67° C.

REFERENCE EXAMPLE 7

Iodomethane (4.5 ml) was added to a stirred mixture of magnesium turnings (1.5 g) and anhydrous ether (45 ml). When the resultant reaction had subsided, the mixture was boiled under reflux for 45 min. The ether was removed by distillation under reduced pressure and the residue was dissolved in dry toluene (15 ml) and 4-carbomethoxy-1-(2,6-dichloro-4-trifluoromethylphenyl)-3-trifluoromethylpyrazole (3.0 g) dissolved in dry toluene (30 ml) was added dropwise with stirring. The resultant mixture was heated at 70°-80° C. for 3 hours, allowed to cool, poured into saturated aqueous ammonium chloride solution and shaken well. The layers were separated and the aqueous layer was extracted with ether (2×30 ml). The combined organic layers were washed with water (30 ml) and evaporated to give a yellow solid (2.7 g). This was dissolved in dichloromethane and a solution of hydrogen peroxide (30%; 5 ml) in conc. sulfuric acid (6.5 ml) was added dropwise. During the addition, the mixture was cooled in an ice-bath. The mixture was then stirred for 5 hours, sulfuric acid (70%; 6 ml) was added and the resultant mixture was stirred for a further 19 hours. Ice was added, then aqueous sodium hydroxide solution (50%) to make the solution alkaline. The solution was washed with dichloromethane and then acidified by addition of hydrochloric acid (2Ml). The aqueous solution was extracted with dichloromethane (3×30 ml) and the combined extracts were dried over magnesium sulfate, filtered, and evaporated to give 1-(2,6-dichloro-4-trifluoromethylphenyl)-4-hydroxy-3-trifluoromethylpyrazole as a pale yellow solid, m.p. 186°-187.5° C.

REFERENCE EXAMPLE 8

5-Amino-4-carbomethoxy-1-(2,6-dichloro-4-trifluoromethylphenyl)-3-trifluoromethylpyrazole (described in PCT patent publication WO 8703-781A; 6.54 g) was dissolved in tetrahydrofuran (100 ml) and tert-butyl nitrite (10 ml) was added to the solution. The mixture was refluxed for 2 hours and then evaporated. The residue was purified by dry-column chromatography (eluant dichloromethane:hexane 3:1) to give 4-carbomethoxy-1-(2,6-dichloro-4-trifluoromethylphenyl)-3-trifluoromethylpyrazole (5.2 g) as a pale yellow solid, m.p. 89.5°-91.5° C.

EXAMPLE 4

Compounds 4,5 and 7

By proceeding in a similar manner to that hereinbefore described in Example 3 but replacing the 1-(2,6-dichloro-4-trifluoromethylphenyl)-4-hydroxy-3-trifluoromethylpyrazole by the hereinafter indicated appropriately substituted pyrazole there was obtained:

1-(2,6-Dichloro-4-trifluoromethylphenyl)-4-difluoromethoxy-3-methylpyrazole in the form of a colorless oil, after dry-column chromatography (eluant dichloromethane: hexane 1:1), from 1-(2,6-dichloro-4-trifluoromethylphenyl)-4-hydroxy-3-methylpyrazole.

5-Bromo-3-cyano-1-(2,6-dichloro-4-trifluoromethylphenyl)-4-difluoromethoxypyrazole in the form of a yellow solid, m.p. 123.5°-125.5° C., from 5-bromo-3-cyano-1-(2,6-dichloro-4-trifluoromethylphenyl)-4l-hydroxypyrazole.

1-(2,6-Dichloro-4-trifluoromethylphenyl)-4-difluoromethoxy-3-nitropyrazole in the form of an off-white solid, m.p. 98°-99.5° C., after medium pressure chromatography (eluant dichloromethane/hexane 7:3), from 1-(2,6-dichloro-4-trifluoromethylphenyl)-4-hydroxy-3-nitropyrazole.

EXAMPLE 5

Compound No. 6

A sample of 5% palladium on charcoal (90 mg) was added to a solution of 3-cyano-1-(2,6-dichloro-4-trifluoromethylphenyl)-4-difluoromethoxy-5l-nitropyrazole (0.4 g) in toluene (30 ml) and the mixture was stirred vigorously and heated to 50° C. under a hydrogen atmosphere for 5 hours. The reaction mixture was filtered through Hi-Flo and the filtrate was evaporated to give 5-amino-3-cyano-1-(2,6-dichloro-4-trifluoromethylphenyl)-4-difluoromethoxypyrazole (0.3 g) as a colorless solid, m.p. 151.5°-154.5° C.

REFERENCE EXAMPLE 9

A solution of 3-carboethoxy-1-(2,6-dichloro-4-trifluoromethylphenyl)-4-hydroxypyrazole in a mixture of 2M aqueous sodium hydroxide (50 ml) and dioxan (50 ml) was heated at 60° C. for 5½ hours whilst chlorodifluoromethane was bubbled through it. The solution was evaporated in vacuo and the residue was partitioned between 2M hydrochloric acid (50 ml) and dichloromethane (50 ml). The aqueous layer was re-extracted with dichloromethane (50 ml and the combined dichloromethane extracts were washed with water (50 ml), dried over anhydrous magnesium sulfate, filtered and evaporated in vacuo to give 3-carboxy-1-(2,6-dichloro-4-trifluoromethylphenyl-4-difluoromethoxypyrazole as a pale yellow solid, m.p. 180°-183° C.

REFERENCE EXAMPLE 10

By proceeding in a similar manner to that hereinbefore described in Reference Example 5 but replacing ethyl 2-(2,6-dichloro-4-trifluoromethylphenylazo)-4-chloroacetoacetate there was obtained:

3-Cyano-1-(2,6-dichloro-4-trifluoromethylphenyl)-4-hydroxypyrazole as a buff colored solid, m.p. 175.5°-177.5° C., after recrystallisation from toluene, from 4-bromo-2-(2,6-dichloro-4-trifluoromethylphenylazo)-3-oxobutanenitrile.

1-(2,6-Dichloro-4-trifluoromethylphenyl)-4-hydroxy-3-nitropyrazole as a brown solid, m.p. 150°-156° C., after medium pressure chromatography (eluant dichloromethane), from 1-chloro-3-(2,6-dichloro-4-trifluoromethylphenylazo)-3-nitroacetone.

REFERENCE EXAMPLE 11

By proceeding in a similar manner to that hereinbefore described in Reference Example 6 but replacing ethyl 4-chloroacetoacetate there was obtained:

2-(2,6-Dichloro-4-trifluoromethylphenylazo)-3-oxobutanenitrile as an orange solid, m.p. 62°-67° C., from cyanoacetone.

1-Chloro-3 (2,6-dichloro-4-trifluoromethylphenylazo)-3-nitroacetone as a yellow solid, m.p. 94°-97° C., from 1-chloro-3-nitroacetone.

REFERENCE EXAMPLE 12

By proceeding in a similar manner to that hereinbefore described in Reference Example 7 but replacing 4-carbomethoxy-1-(2,6-dichloro-4-trifluoromethylphenyl)-3-trifluoromethylpyrazole there was obtained:

1-(2,6-Dichloro-4-trifluoromethylphenyl)-4-hydroxy-3-methylpyrazole as a cream solid, m.p. 237°-239° C., after dry-column chromatography (eluant dichloromethane) and trituration with hexane, from 1-(2,6-dichloro-4-trifluoromethylphenyl)-4-carboethoxy-3-methylpyrazole.

REFERENCE EXAMPLE 12

By proceeding in a similar manner to that hereinbefore described in Reference Example 8 but replacing 5-Amino-4-carbomethoxy-1-(2,6-dichloro-4-trifluoromethlyphenyl)-3-trifluoromethylpyrazole there was obtained:

4-Carboethoxy-1-(2,6-dichloro-4-trifluoromethylphenyl)-3-methylpyrazole as an off-white solid, m.p. 65°-67° C., after medium pressure chromatography (eluant dichloromethane) and trituration with hexane, from 5-Amino-4-carboethoxy-1-(2,6-dichloro-4-trifluoromethylphenyl)-3-methylpyrazole (described in PCT patent publication WO 8703-781-A).

REFERENCE EXAMPLE 13

A mixture of 3-cyano-1-(2,6-dichloro-4-trifluoromethylphenyl)-4-hydroxypyrazole (1.0g) and N-bromosuccinimide (0.55g) in chloroform (20ml) was stirred at room temperature for 75 minutes, then washed with water (3×20 ml), filtered through phase-separation paper and evaporated. The residue was purified by dry-column chromatography (eluant ether: hexane 1:1 then 3:1) to give 5-bromo-3-cyano-1-(2,6-dichloro-4-trifluoromethylphenyl)-4-hydroxypyrazole as a buff colored solid, m.p. 145°-151° C.

REFERENCE EXAMPLE 14

A solution of bromine (2.2 ml) in chloroform (20 ml) was added dropwise to a stirred solution of 2-(2,6-dichloro-4-trifluoromethylphenylazo)-3-oxobutanenitrile (13.0g) in chloroform (20 ml) maintained at 50° C. The solution was then refluxed for 20 minutes, cooled, washed with water (4×50 ml), dried over magnesium sulfate, filtered and evaporated to give 4-bromo-2-(2,6-dichloro-4-trifluoromethylphenylazo)-3-oxobutanenitrile (16.0g) as a brown oil.

REFERENCE EXAMPLE 15

Fuming nitric acid (5 ml) was added to an ice-cooled solution of 3-cyano-1-(2,6-dichloro-4-trifluoromethylphenyl)-4-difluoromethoxypyrazole (1.5g) in concentrated sulfuric acid (20 ml). The mixture was stirred at room temperature for 3 hours then poured into ice/water and extracted into dichloromethane (3×50 ml). The combined dichloromethane extracts were washed with water (30 ml), filtered through phase-separation paper and evaporated in vacuo. The resultant gum was purified by dry-column chromatography (eluant ether:hexane 1:3) t give 3-cyano-1-(2,6-dichloro-4-trifluoromethylphenyl)-4-difluoromethoxy-5-nitropyrazole (0.3g) as a yellow solid, m.p. 72.5°-74° C.

According to a feature of the present invention, there is provided a method for the control of arthropod, plant nematode, helminth or protozoan pests at a locus which comprises the treatment of the locus (e.g. by application or administration) with an effective amount of a compound of general formula (I), or a pesticidally acceptable salt thereof, wherein the various symbols are as hereinbefore defined. The compounds of general formula (I) may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, grats, equines, swine, poultry, dogs, cats and fishes, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata* and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Musca spp., Hypoderma spp., Gasterophilus spp., Simulium spp.); Hemiptera (e.g. Triatoma spp.); Phthiraptera (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastrointestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus battus, Ostertagia circumcincta. Trichostrongylus axei,* Cooperia spp. and Hymenolepis nana; in the control and treatment of protozoal diseases caused by, for example, Eimeria spp. e.g. *Eimeria tenella, Eimeria acervulina. Eimeria brunetti, Eimeria maxima* and *Eimeria necatrix, Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example Reticulitermes spp.,Heterotermes spp., Coptotermes spp.; in agriculture, against adults, larvae and eggs of Lepidoptera (butterflies and moths), e.g. Heliothis spp. such as *Heliothis virescens* (tobacco budworm), *Heliothis armigera* and *Heliothis zea,* Spodoptera spp. such as *S.exempta, S.littoralis* (Egyptian cotton worm), *S.eridania* (southern army worm), *Mamestra configurata* (bertha army worm); Earias spp. e.g. *E.insulana* (Egyptian bollworm), Pectinophora spp. e.g. *Pectinophora gossypiella* (pink bollworm), Ostrinia spp. such as *O.nubilalis* (European cornborer), Trichoplusia ni (cabbage looper), Pieris spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond back moth); against adult and larvae of Coleoptera (beetles) e.g. *Hypotheneus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); against Hemiptera e.g. Psylla spp., Bemisia spp.,Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseudococcus spp., Helopeltis spp. (mosquito bugs), Lygus spp., Dysdercus spp., Oxycarenus spp., Nezara spp.; Hymenoptera e.g. Athalia spp. and Cephus spp. saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as Thrips tabaci; Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphagotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry, horticulture either directly or by spreading bacterial, viral, mycoplasma or fungal diseases of the plants, root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A.- besseyi*); stem and bulb eelworms such as Ditylenchus spp. (e.g. *D. dipsaci*).

The invention also provides a method for the control of arthropod o nematode pests of plants which comprises the application to the plants or to the medium in which they grow of an effective amount of a compound of general formula (I) or a pesticidally acceptable salt thereof.

For the control of arthropods and nematodes, the active compound is generally applied to the locus in which arthropod or nematode infestation is to be controlled at a rate of about 0.1 kg to about 25kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 1 g to 1000g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula (I) may be applied in solid or liquid compositions to the soil principally t control those nematodes dwelling therein but also to the foliage principally to control those nematodes attacking the aerial parts of the plants (e.g. Aphelenchoides spp. and Ditylenchus spp. listed above).

The compounds of general formula (I) are of value in controlling pests which feed on parts of the plant remote from the point of application, e.g. leaf feeding insects are killed by the subject compounds applied to roots.

In addition the compounds may reduce attacks on the plant by means of antifeeding or repellent effects.

The compounds of general formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soybean, oil seed rape), sugar cane, grassland and forage such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts, vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids) or termites, for example Reticulitermes spp., Heterotermes spp., Coptotermes spp..

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of general formula (I) are particularly useful in controlling arthropods, helminths or protozoa which are present inside domestic host animals or which feed in or on the skin or suck the blood of the animal, for which purpose they may be administered orally, parentally, percutaneously or topically. Coccidiosis, a disease caused by infections by protozoan parasites of the genus Eimeria, is an important potential cause of economic los in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection.

Administration of a small amount of a compound of general formula (I) or a pesticidally acceptable salt thereof preferably by combination with poultry feed is effective in preventing or greatly reducing the incidence of coccidioais. The compounds are effective against both the cecal form (caused by *E. tenella*) and the intestinal forms (principally caused by *E. acervulina, E. brunetti, E. maxima* and *E. necatrix*).

The compounds of general formula (I) also exert an inhibitory effect on the oocysts by greatly reducing the number and or the sporulation of those produced.

The compositions hereinafter described for topical application to man and animals and in the protection of stored products, household goods, property and areas of the general environment may, in general, alternatively be employed for application to growing crops and crop growing loci and as a seed dressing.

Suitable means of applying the compounds of general formula (I) include: to persons or animals infested by or exposed to infestation by arthropods, helminths or protozoa, by parental, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their faeces; to growing crops as foliar sprays, dusts, granules, fogs and foams; also as suspensions of finely divided and encapsulated compounds of general formula (I); as soil and root treatments by liquid drenches, dusts, granules, smokes and foams and as seed dressings by liquid slurries and dusts.

The compounds of general formula (I) may be applied to control arthropods, helminths or protozoa in compositions of any type known to the art suitable for internal or external administration to vertebrates or application for the control of arthropods in any premises or indoor or outdoor area, containing as active ingredient at least one compound of general formula (I) in association with one or more compatible diluents or adjuvants appropriate for the intended use. All such compositions may be prepared in any manner known to the art.

Compositions suitable for administration to vertebrates or man include preparations suitable for oral, parental, percutaneous, e.g. pour-on, or topical administration.

Compositions for oral administration comprise one or more of the compounds of general formula (I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parental administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Solid or liquid baits suitable for controlling arthropods comprise one or more compounds of general formula (I) and a carrier or diluent which may include a food substance or some other substance to induce consumption by the arthropod.

Liquid compositions include water miscible concentrates, emulsifiable concentrates, flowable suspensions, wettable or soluble powders containing one or more compounds of general formula (I) which may be used to treat substrates or sites infested or liable to infestation by arthropods including premises, outdoor or indoor storage or processing areas, containers or equipment and standing or running water.

Solid homogeneous or heterogeneous compositions containing one or more compounds of general formula (I), for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solutions or dispersions suitable for spraying, fogging and low- or ultra-low volume spraying may also be used.

Suitable solid diluents which may be used in the preparation of compositions suitable for applying the compounds of general formula (I) include aluminum silicate, kieselguhr, corn husks, tricalcium phosphate, powdered cork, absorbent carbon black, magnesium silicate, a clay such as kallin, bentonite or attapulgite, and water soluble polymers and such solid compositions may, if desired, contain one or more compatible wetting, dispersing, emulsifying or coloring agents which, when solid, may also serve as diluent.

Such solid compositions, which may take the form of dusts, granules or wettable powders, are generally prepared by impregnating the solid diluents with solutions of the compound of general formula (I) in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g. gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octyl-phenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of general formula (I) may take the form of solutions, suspensions and emulsions of the compounds of general formula (I) optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of general formula (I) may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavoring agents, dyes and auxiliary therapeutic agents, e.g. trace elements. These may be designed to improve potency, persistence, safety, uptake where desired, spectrum of pests controlled or to enable the composition to perform other useful functions in the same animal or area treated. Examples of other pesticidally-active compounds which may be included in, or used in conjunction with, the compositions of the present invention are:- acephate, chlorpyrifos, demeton-S-methyl, disulfoton, ethoprofos, fenitrothion, malathion, monocrotophos, parathion, phosalrne, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetridazole.

The compositions for application to control arthropod, plant nematode, helminth or protozoan pests usually contain from 0.00001% to 95%, more particularly from 0.0005% to 50%, by weight of one or more compounds of general formula (I) or of total active ingredients (that is to say the compound(s) of general formula (I) together with other substances toxic to arthropods and plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, more particularly from 0.001% to 10%, by weight of one or more compounds of general formula (I). For administration to animals orally or parentally, including percutaneously solid and liquid compositions normally contain from 0.1% to 90% by weight of one or more compound of general formula (I). Medicated feedstuffs normally contain from 0.001% to 3% by weight of one or more compounds of general formula (I). Concentrates and supplements for mixing with feedstuffs normally contain from 5% to 90%, and preferably from 5% to 50%, by weight of one or more compounds of general formula (I). Mineral salt licks normally contain from 0.1% to 10% by weight of one or more compounds of general formula (I).

Dusts and liquid compositions for application to livestock, persons, goods, premises or outdoor areas may contain 0 0001% to 15%, and more especially 0.005% to 2.0%, by weight of one or more compounds of general formula (I). Suitable concentrations in treated waters are between 0.0001 ppm and 20 ppm, and more especially 0.001 ppm to 5.0 ppm. of one or more compounds of general formula (I) and may also be used therapeutically in fish farming with appropriate exposure times. Edible baits may contain from 0.01% to 5% and preferably 0.01% to 1.0%, by weight of one or more compounds of general formula (I).

When administered to vertebrates parentally, orally or by percutaneous or other means, the dosage of compounds of general formula (I) will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parental administration. By use of sustained release formulations or devices, the daily doses required over a period of months may be combined and administered to animals on a single occasion.

The following Composition Examples illustrate compositions for use against arthropod, plant nematode, helminth or protozoan pests which comprise, as active ingredient, compounds of general formula (I). The compositions described in Composition Examples 1 to 6 can each be diluted in water to give a sprayable composition at concentrations suitable for use in the field.

COMPOSITION EXAMPLE 1

A water soluble concentrate was prepared from

| | |
|---|---|
| 3-Cyano-1-(2,6-dichloro-4-trifluoromethyl-phenyl)-4-difluoromethoxypyrazole | 7% w/v |
| Ethylan BCP | 10% w/v |
| and N-methylpyrrolidone | to 100% by volume | by dissolving the Ethylan BCP in a portion of N-methylpyrrolidone, and then adding the active ingredient with heating and stirring until dissolved.

The resulting solution was made up to volume by adding the remainder of the solvent.

COMPOSITION EXAMPLE 2

An emulsifiable concentrate was prepared from

| | |
|---|---|
| 3-Cyano-1-(2,6-dichloro-4-trifluoromethyl-phenyl)-4-difluoromethoxypyrazole | 7% w/v |
| Soprophor BSU | 4% w/v |
| Arylan CA | 4% w/v |
| N-methylpyrrolidone | 50% w/v |
| and Solvesso 150 | to 100% by volume | by dissolving Soprophor BSU, Arylan CA and the active ingredient in N-methylpyrrolidone, and then adding Solvesso 150 to volume.

COMPOSITION EXAMPLE 3

A wettable powder was prepared from

| | |
|---|---|
| 3-Cyano-1-(2,6-dichloro-4-trifluoromethyl-phenyl)-4-difluoromethoxypyrazole | 40% w/w |
| Arylan S | 2% w/w |
| Darvan No. 2 | 5% w/w |
| and Celite PF | to 100% by weight | by mixing the ingredients, and grinding the mixture in a hammer-mill to a particle size less than 50 microns.

COMPOSITION EXAMPLE 4

An aqueous flowable formulation was prepared from

| | |
|---|---|
| 3-Cyano-1-(2,6-dichloro-4-trifluoromethyl-phenyl)-4-difluoromethoxypyrazole | 30% w/v |
| Ethylan BCP | 1% w/v |
| Sopropon T36 | 0.2% w/v |
| Ethylene glycol | 5% w/v |
| Rhodigel 23 | 0.15% w/v |
| and Water | to 100% by volume | by intimately mixing the ingredients and grinding in a bead mill until the median particle size was less than 3 microns.

COMPOSITION EXAMPLE 5

An emulsifiable suspension concentrate was prepared from

| | |
|---|---|
| 3-Cyano-1-(2,6-dichloro-4-trifluoromethyl-phenyl)-4-difluoromethoxypyrazole | 30% w/v |
| Ethylan BCP | 10% w/v |
| Bentone 38 | 0.5% w/v |
| and Solvesso 150 | to 100% by volume | by intimately mixing the ingredients and grinding in a bead mill until the median particle size was less than 3 microns.

COMPOSITION EXAMPLE 6

Water dispersible granules were prepared from

| | |
|---|---|
| 3-Cyano-1-(2,6-dichloro-4-trifluoromethyl-phenyl) 4-difluoromethoxypyrazole | 30% w/w |
| Darvan No. 2 | 15% w/w |
| Arylan S | 8% w/w |
| and Celite PF | to 100% by weight | by mixing the ingredients, micronising in a fluid-energy mill, and then granulating in a rotating pelletiser by spraying on sufficient water (up to 10% w/w). The resulting granule were dried in a fluid-bed drier to remove excess water.

Descriptions of commercial ingredients used in the foregoing Composition Examples

| | |
|---|---|
| Ethylan BCP | nonylphenol ethylene oxide condensate |
| Soprophor BSU | condensate of tristyrylphenol and ethylene oxide |
| Arylan CA | 70% w/v solution of calcium dodecylbenzenesulphonate |
| Solvesso 150 | light $C_{10}$-aromatic solvent |
| Arylan S | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38 | organic derivative of magnesium montmorillonite |

COMPOSITION EXAMPLE 7

A dusting powder may be prepared by intimately mixing:

| | |
|---|---|
| 3-Cyano-1-(2,6-dichloro-4-trifluoromethyl-phenyl)-4-difluoromethoxypyrazole (weight/weight) | 1 to 10% w/w |
| Talc superfine | to 100% by weight |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

COMPOSITION EXAMPLE 8

An edible bait may be prepared by intimately mixing:

| | |
|---|---|
| 3-Cyano-1-(2,6-dichloro-4-trifluoromethylphenyl)-4-difluoromethoxypyrazole | 0.1 to 1.0% w/w |
| Wheat flour | 80% w/w |
| Molasses | to 100% w/w |

This edible bait may be distributed at a locus, for example domestic and industrial premises, e.g. kitchens, hospitals or stores, or outdoor areas, infested by arthropods, for example ants, locusts, cockroaches and flies, to control the arthropods by oral ingestion.

COMPOSITION EXAMPLE 9

A solution may be prepared containing:

| | |
|---|---|
| 3-Cyano-1-(2,6-dichloro-4-trifluoromethylphenyl)-4-difluoromethoxypyrazole (weight/volume) | 15% w/v |
| Dimethylsulphoxide | to 100% by volume | by dissolving the pyrazole derivative in a portion of the dimethyl- sulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 micrometer pore size), by parental injection, at a rate of application of from 1.2 to 12 ml of solution per 100 kg of animal body weight.

COMPOSITION EXAMPLE 10

A wettable powder may be formed from:

| | |
|---|---|
| 3-Cyano-1-(2,6-dichloro-4-trifluoromethylphenyl)-4-difluoromethoxypyrazole | 50% w/w |
| Ethylan BCP (a nonylphenol/ethylene oxide condensate containing 9 moles of ethylene oxide per mol of phenol) | 5% w/w |
| Aerosil (silicon dioxide of microfine-particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder, which may be diluted with water to a concentration of from 0.001% to 2% w/v of the pyrazole compound and applied to a locus of infestation by arthropods, for example dipterous larvae, or plant nematodes by spraying, or to domestic animals infested by, or at risk of infestation by, arthropods, helminths or protozoa, by spraying or dipping, or by oral administration as drinking water, to control the arthropods, helminths or protozoa.

COMPOSITION EXAMPLE 11

A slow release bolus may be formed from granules containing a density agent, binder, slow-release agent and 3-cyano-1-(2,6-dichloro-4-trifluoromethylphenyl)-4-difluoromethoxypyrazole compound at varying percentage compositions. By compressing the mixture a bolus with a specific gravity of 2 or more can be formed and may be administered orally to ruminant domestic animals for retention within the reticulo-rumen to give a continual slow release of pyrazole compound over an extended period of time to control infestation of the ruminant domestic animals by arthropods, helminths or protozoa.

COMPOSITION EXAMPLE 12

A slow release composition may be prepared from:

| | |
|---|---|
| 3-Cyano-1-(2,6-dichloro-4-trifluoromethylphenyl)-4-difluoromethoxypyrazole | 0.5 to 25% w/w |
| polyvinylchloride base | to 100% w/w | by blending the polyvinylchloride base with the pyrazole compound and a suitable plasticiser, e.g. dioctyl phthalate, and melt-extruding or hot-molding the homogeneous composition into suitable shapes, e.g. granules, pellets, brickettes or strips, suitable, for example, for addition to standing water or, in the case of strips, fabrication into collars or ear-tags for attachment to domestic animals, to control insect pests by slow release of the pyrazole compound.

Similar compositions may be prepared by replacing the 3-cyano-1-(2,6-dichloro-4-trifluoromethylphenyl)-4-difluoromethoxypyrazole in the Composition Examples by the appropriate quantity of any other compound of general formula (I).

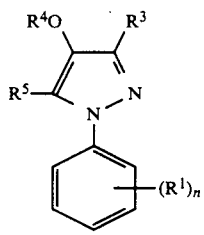

I

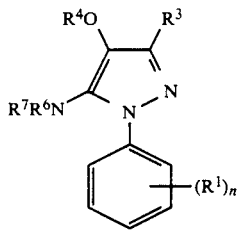

IB

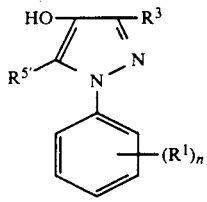

II

-continued
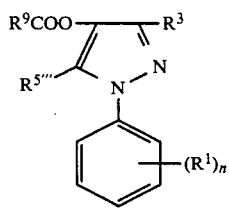 VI
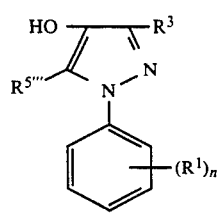 VII
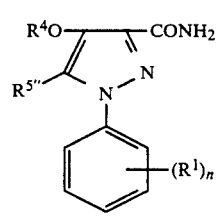 VIII
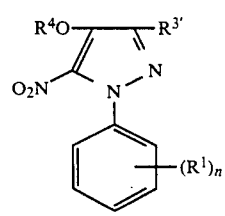 IX
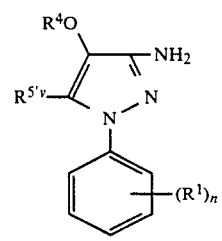 X
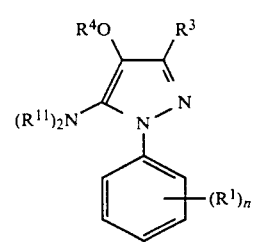 XIII
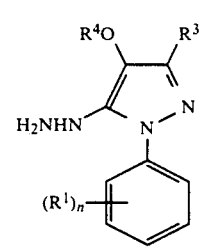 XVI
-continued
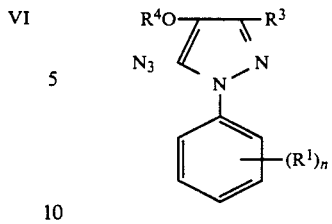 XVII
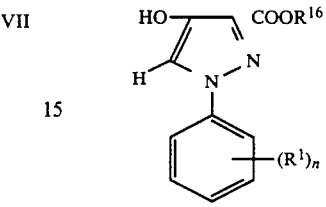 XVIII
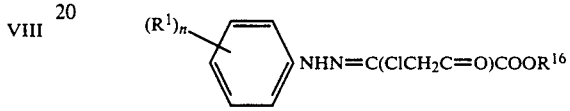 XIX
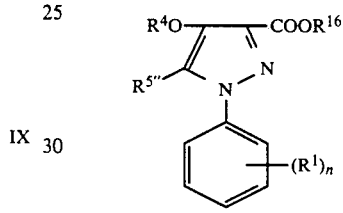 XX
 XXI
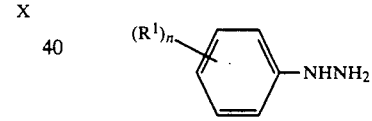 XXIV
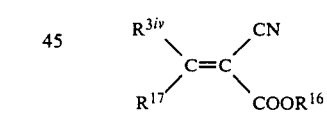 XXIII
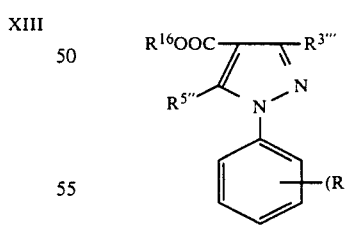 XXII
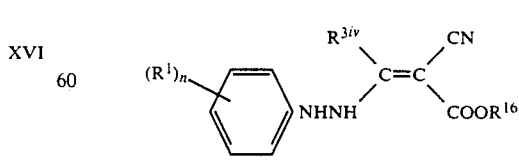 XXV
We claim:
1. An N-phenylpyrazol-4-yl ether derivative having the formula:

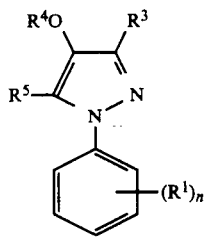

wherein $R^1$ is a halogen atom, a straight- or branched-chain alkyl or alkoxy radical containing from 1 to 4 carbon atoms, a substituted such alkyl or alkoxy radical bearing at least one halogen, a straight- or branched-chain alkylthio or alkylsulphinyl group containing from 1 to 4 carbon atoms which is substituted by at least one halogen, a nitro or cyano group or a straight- or branched-chain alkylsulphonyl group containing from 1 to 4 carbon atoms, or a substituted such alkylsulphonyl group bearing at least one halogen, and n is an integer from 1 to 5 inclusive, $R^3$ is hydrogen, a halogen, a cyano or nitro group, a straight- or branched-chain alkyl group $R^2$ containing from 1 to 4 carbon atoms, or a substituted such alkyl group bearing at least one halogen, $R^4$ is a straight- or branched-chain alkyl, alkenyl or alkynyl group containing up to 6 carbon atoms which is substituted by at least one halogen selected from flourine, chlorine, bromine and iodine, $R^5$ is hydrogen or an amino group $NR^6R^7$ wherein $R^6$ and $R^7$, which may be the same or different, are each hydrogen or a straight- or branched-chain alkyl group containing from 1 to 6 carbon atoms, the formyl group, a straight- or branched-chain alkanoyl group containing from 2 to 7 carbon atoms, or a substituted such alkanoyl group bearing at least one halogen, a straight- or branched-chain alkoxycarbonyl group containing from 2 to 7 carbon atoms, a substituted such alkoxycarbonyl group bearing at least one halogen, or $R^6$ and $R^7$ together form a 5 or 6 membered cyclic imide with the nitrogen atom to which they are attached, or $R^5$ represents a straight- or branched-chain alkoxymethyleneamino group containing from 2 to 5 carbon atoms, or a substituted such alkoxymethyleneamino bearing on the methylene carbon a straight- or branched-chain alkyl group containing from 1 to 4 carbon atoms, or $R^5$ is halogen or a group Het selected from pyrrol-1-yl, pyrazol-1-yl, 1,2,3-triazol-1-yl or 1,2,4-triazol-4-yl, piperidino, pyrrolidino, morpholino and N-alkylpiperazino or a substituted such Het group bearing at least one $C_1$-$C_4$ alkyl or phenyl or when $R^5$ is a piperidino, pyrrolidino, morpholino or N-alkylpiperazino group, an acceptable acid addition salt thereof.

2. A compound according to claim 1 wherein $(R^1)_n$ is a 2,4,6-trichloro, 2,6-dichloro-4-trifluoromethyl or 2,6-dichloro-4-trifluoromethoxy substitution of the phenyl group.

3. A compound according to claim 1 wherein $R^4$ is a straight- or branched-chain alkyl group having 1 to 4 carbon atoms or a straight- or branched-chain alkenyl or alkynyl group having 2 to 4 carbon atoms, each of which is substituted by at least one halogen which may be the same or different and $R^3$ is a halogen atom or a nitro or cyano group.

4. A compound according to claim 3 wherein $R^3$ is a cyano group.

5. A compound according to claim 1 wherein the alkyl group $R^2$ is perhalogenated.

6. A compound according to claim 1 comprising:
3-cyano-4-(2-chloro-1,1,2-trifluoroethoxy)-1-(2,6-dichloro-4-trifluoromethylphenyl)pyrazole,
3-cyano-1-(2,6-dichloro-4-trifluoromethylphenyl)-4-difluoromethoxypyrazole,
1-(2,6-dichloro-4-trifluoromethylphenyl)-4-difluoromethoxy-3-trifluoromethylpyrazole,
1-(2,6-dichloro-4-trifluoromethylphenyl)-4-difluoromethoxy-3-methylpyrazole,
5-bromo-3-cyano-1-(2,6-dichloro-4-trifluoromethylphenyl)-4-difluoromethoxypyrazole,
5-amino-3-cyano-1-(2,6-dichlorol-4-trifluoromethylphenyl)-4-difluoromethoxypyrazole, or
1-(2,6-dichloro-4-trifluoromethylphenyl)-4-difluoromethoxy-3-nitropyrazole.

7. A process for the preparation of a compound according to claim 1, wherein $R^5$ is hydrogen, halogen or a $NR^6R^7$ group wherein $R^6$ and $R^7$ are acetyl or alkyl groups, comprising the reaction of a compound of the general formula:

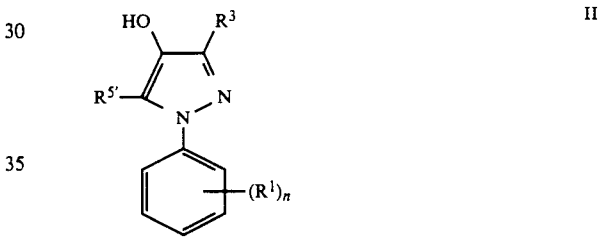

wherein $R^{5'}$ is hydrogen or halogen or a $NR^{6'}R^{7'}$ group wherein $R^{6'}$ and $R^{7'}$ are acetyl or alkyl groups, or an alkali metal salt thereof, with a reagent $R^4X'$ wherein $X'$ represents a halogen atom, or a compound of general formula:

wherein $X^2$ represents a fluorine, chlorine or bromine atom and $R^8$ is as defined for $X^2$ or a trifluoromethyl group.

8. An arthropodicidal, plant nematocidal, anthelmintic or anti-protozoal composition of matter, comprising an effective amount of an N-phenylpyrazol-4-yl ether derivative according to claim 1, or an acceptable acid addition salt thereof, in combination with one or more compatible diluents or carriers.

9. A method for controlling arthropod, plant nematode, helminth or protozoal pests at a locus, comprising treating the locus with an effective amount of an N-phenylpyrazol-4-yl ether derivative according to claim 1, or with an acceptable acid addition salt thereof.

* * * * *